United States Patent [19]

Ruf

[11] Patent Number: 5,068,373

[45] Date of Patent: Nov. 26, 1991

[54] METHOD FOR THE PREPARATION OF ANHYDROUS TIN-(IV)-CARBOXYLATES

[75] Inventor: Erich Ruf, Essen-Haarzopf, Fed. Rep. of Germany

[73] Assignee: Th. Goldschmidt AG, Essen, Fed. Rep. of Germany

[21] Appl. No.: 647,403

[22] Filed: Jan. 29, 1991

[30] Foreign Application Priority Data

Feb. 6, 1990 [DE] Fed. Rep. of Germany ....... 4003488

[51] Int. Cl.$^5$ ................................................ C07F 7/22
[52] U.S. Cl. ................................................ 556/105
[58] Field of Search ........................................ 556/105

[56] References Cited

U.S. PATENT DOCUMENTS 3,162,660 12/1964 Crayton .............................. 260/414

FOREIGN PATENT DOCUMENTS 0015008 7/1965 Japan ................................ 556/105
1175983 7/1989 Japan ................................ 556/105

Primary Examiner—José G. Dees
Assistant Examiner—Porfirio Nazario-Gonzalez
Attorney, Agent, or Firm—Toren, McGeady & Associates

[57] ABSTRACT

A method is disclosed for the preparation of anhydrous tin-(IV)-carboxylate. Metallic tin or Sn-(II)-acetate is reacted with an excess of acetic acid anhydride under agitation and at temperatures of 50° to 150° C. Oxygen is passed through the reaction mixture or an oxygen yielding agent is added thereto. The tin-(IV)-acetate thus formed, which is useful, per se, is separated from the reaction mixture and further reacted with a carboxylic acid with more than four carbon atoms or an acid anhydride corresponding to said carboxylic acid. The reaction is carried out at temperatures of about 80° to 150° C. and the liberated acetic acid anhydride or acetic acid is removed by distillation under vacuum.

6 Claims, No Drawings

METHOD FOR THE PREPARATION OF ANHYDROUS TIN-(IV)-CARBOXYLATES

FIELD OF INVENTION

The invention generally relates to tin-(IV)-carboxylates and is particularly directed to a method for the preparation of anhydrous tin-(IV)-carboxylate.

BACKGROUND INFORMATION AND PRIOR ART

A method for the preparation of tin-(II)-acetate is disclosed in the literature. Thus, for example, Gmelin, 8th Ed., 1975, No. 46, Part C 2, pp. 220–221 discloses the reaction of metallic tin and glacial acetic acid wherein the reaction is permitted to proceed for 80 to 90 hours under reflux conditions and in an inert gas atmosphere. Tin-(II)-acetate is the sole reaction product, but no tin-(IV)-acetate is formed.

In order to produce tin-(IV)-acetate, expensive intermediate compounds first have to be prepared such as, for example, thallium acetate. The thallium acetate is reacted in acetic acid anhydride with tin-(IV)-iodide or tin-(IV)-bromide to obtain tin-(IV)-acetate. This procedure is exceedingly cumbersome and, from an economics point of view, requires substantial expenditure.

OBJECTS OF THE INVENTION

It is a primary object of the present invention to provide a method for the production of anhydrous tin-(IV)-carboxylates which is economical and simple to carry out.

Generally, it is an object of the invention to improve on the art of producing anhydrous tin-(IV)-carboxylate.

SUMMARY OF THE INVENTION

Pursuant to the invention, anhydrous tin-(IV)-carboxylate is prepared in a two-stage process wherein, in the first stage, tin-(IV)-acetate is prepared which, in the second stage, is transferred into the desired carboxylate by being reesterified with the corresponding acid anhydrides or carboxylic acids. Briefly, metallic tin or Sn-(II)-acetate is treated with an excess of acetic acid anhydride, the reaction mixture being stirred and heated to temperatures of 50° to 150° C. while passing oxygen through the mixture or by adding an oxygen yielding agent. The tin-(IV)-acetate thus obtained is separated and then reacted in known manner with carboxylic acids with more than four carbon atoms or the corresponding organic acid anhydrides at a temperature of 80° to 150° C. The liberated acetic acid anhydride or acetic acid is then removed by distillation under vacuum conditions.

1. First method stage

The metallic tin, in order to increase its reactivity, is preferably used in the form of a fine powder. The reaction of the metallic tin or of the Sn-(II)-acetate takes place at 50° to 150° C. The preferred temperature range is 80° to 130° C. It has been found to be advantageous to carry out the reaction in the presence of acetic acid as solvent.

The oxidation of the tin into the four-valent stage is carried out with oxygen or oxygen yielding agents.

As oxygen yielding agent, it is advantageous to use an aqueous hydrogen peroxide solution. In order to obtain the desired anhydrous tin-(IV)-acetate, it is necessary to transfer the water which has been introduced by means of the hydrogen peroxide solution, into acetic acid by adding corresponding amounts of acetic acid anydride. The reaction mixture is cooled after a reaction period of 5 to 8 hours and the precipitated tin-(IV)-acetate is removed by filtration and dried. The white anhydrous tin-(IV)-acetate precipitates in a yield of 70 to 80%. By concentrating and/or cooling the mother liquor, additional tin-(IV)-acetate can be recovered so that the total yield can be increased to about 97%.

2. Second Method Stage

The second method stage comprises the reaction of the anydrous tin-(IV)-acetate, obtained in the first stage, with carboxylic acids with more than four carbon atoms or the corresponding organic acid anhydrides at temperatures of 80° to 150° C. while, at the same time, distilling off the liberated acetic acid anhydride or acetic acid. The removal by distillation is accomplished at reduced pressure. In this manner, the corresponding tin-(IV)-carboxylates are obtained in simple manner in anhydrous form.

In a preferred embodiment, the reaction of tin-(IV)-acetate with the organic acid anhydride or the organic acid is performed at temperatures of 100° to 110° C. under slight vacuum conditions. The tin-(IV)-carboxylate corresponding to the organic acid anhydride used is obtained in this manner in substantially quantitive manner.

Organic acid anhydrides of carboxylic acids with more than four carbon atoms to be used pursuant to the invention are, among others, propionic acid anhydride, butyric acid anhydride and valeric acid anhydride. Particularly preferred are the anhydrides of the higher molecular fatty acids such as, for example, of lauric acid, palmitic acid or stearic acid. As carboxylic acids with more than four carbon atoms, valeric acid, caprylic acid or undecanoic acid are suitable. Also in this instance the higher molecular acids such as myristic acid, palmitic acid or steric acid are preferably used. Examples for unsaturated fatty acids are the oleic acid and the linoleic acid. Generally, fatty acids with up to 22 carbon atoms or their anhydrides are preferred.

The anhydrous tin-(IV)-acetate obtained in the first stage of the inventive method can be used as the tin basis compound in the application of electrically conductive and infrared reflecting layers on glass and ceramic surfaces. Moreover, the tin-(IV)-acetate, as such, or in suitable formulations, is useful for chemical preservation of glass surfaces. As to the higher molecular tin-(IV)-carboxylates, these are suitable as gliding and lubricating agents as well as agents facilitating the compression of sintered materials, particularly on the basis of bronze. Another field of application for tin-(IV)-acetate is the production of tin-containing metal oxane compounds.

The inventive method is described in further detail in the following examples, it being understood that these examples are given by way of illustration and not limitation. The production of the anhydrous tin-(IV)-acetate (stage 1 to the inventive method) is described in Examples 1–4, while Examples 5–11 are concerned with the production of tin-(IV)-carboxylate having more than four carbon atoms (stage 2 of the inventive procedure).

EXAMPLE 1

The procedure was carried out in a 500 ml four-neck flask fitted with thermometer, cooler, stirrer and gas inlet pipe.

35.6 gram tin powder, 67.3 gram acetic acid anhydride, and
225.0 gram acetic acid
are introduced into the flask, and the mixture is heated, under stirring, to about 110° C. Oxygen is passed through the heated mixture. The reaction time with constant introduction of oxygen amounts to about 6.5 hours. Subsequently, the acetic acid is removed by distillation by means of a rotation evaporator at about 20 mm Hg at about 60° C. under a vacuum. The tin-(IV)-acetate obtained in this manner is admixed with 300 gram acetic acid anhydride and the mixture is briefly heated to about 100° C. Subsequently, acetic acid anhydride is removed by distillation in a rotation evaporator under vacuum conditions at 10 mm Hg/60° C. The anhydrous tin-(IV)-acetate obtained in this manner is washed twice with about 75 ml ethylacetate each and dried in the rotation evaporator.

The yield is 103.7 gram anhydrous tin-(IV)-acetate.

EXAMPLE 2

This experiment was also carried out in a 500 ml, four-neck flask fitted with thermometer, cooler, stirrer and gas introduction pipe.
23.7 gram tin powder and
255.0 gram acetic acid anhydride
are introduced into the flask and the mixture is heated under stirring up to reflux temperature. Subsequently, oxygen is passed through the mixture at 120° C. After about 1 hour, 300 gram acetic acid anhydride is added to the mixture and the introduction of oxygen is continued at about 120° C. The reaction time amounts to about 4 hours. The solution thus obtained is cooled down to 0° C. and is filtered off through a sintered glass frit filter. The filter residue obtained in this manner is washed with about 75 ml ethylacetate and dried in the rotation evaporator.

The yield is 52 gram anhydrous tin-(IV)-acetate.

EXAMPLE 3

This experiment was carried out in a 2 liter, 4-neck flask fitted with thermometer, stirrer, cooler and drop funnel.
1020 gram acetic acid anhydride and
95 gram tin powder
are added to the flask, and the mixture is heated to about 140° C. After 1 hour, the mixture is brought to a temperature of about 110° to 120° C. and 88 gram hydrogen peroxide solution (70%) is added in dropwise manner. After about 3 hours of adding the hydrogen peroxide solution in dropwise manner, the reaction mixture is admixed with 300 gram acetic acid anhydride and is stirred for 1 hour at 120° C. and thereafter until room temperature has been reached. The tin-(IV)-acetate obtained in this manner is removed by filtration. The filtrate solution is cooled down to about 4° C., whereby additional tin-(IV)-acetate is separated. The separated tin-(IV)-acetate is also removed by filtration and, together with the first filtrate amount, is washed three times with about 75 ml of butyl acetate. The washed tin-(IV)-acetate is subsequently dried at room temperature in vacuum at 2 mm Hg in a rotation evaporator.

The yield is 227.6 gram anhydrous tin-(IV)-acetate.

EXAMPLE 4

The experiment was carried out in a 1 liter four-neck flask fitted with thermometer, cooler, stirrer and gas introduction pipe.
47.3 gram tin-(II)-acetate,
44.9 gram acetic acid anhydride, and
150.1 gram acetic acid
are introduced into the flask, and the mixture is heated, under stirring, to 115° C. Oxygen is passed through the heated mixture. The reaction time amounts to about 2.5 hours. Subsequently, the reaction mixture is liberated at the rotation evaportor at about 60° to 80° C. under a vacuum conditions (<10 mbar) from the liquid components. The amount of tin-(II)-compounds is about 0.1%.

The yield is 65.4 gram anhydrous tin-(IV)-acetate.

EXAMPLE 5

This experiment was carried out in a 250 ml, four-neck flask fitted with thermometer, cooler and stirrer.
35.5 gram tin-(IV)-acetate and
113.8 gram stearic acid
are introduced into the flask and the mixture is heated to 100° C. under slight vacuum conditions. At about 70° C. a clear melt is obtained. The acetic acid which is formed is removed by distillation under vacuum conditions (20 to 2 mm Hg/100° C.) and is received in cooling traps. The acetic acid has been quantitatively distilled off in about 6.5 hours.

The yield is 124.8 gram tin-(IV)-stearate.

EXAMPLE 6

This experiment was also carried out in a 250 ml, four-neck flask fitted with thermometer, cooler and stirrer.
35.5 gram tin-(IV)-acetate and
110.2 gram stearic acid anhydride
are introduced into the flask and the mixture is heated to 100° C. under slight vacuum conditions. At about 70° C. a clear melt is obtained. Acetic acid anhydride is subsequently removed by distillation under vacuum conditions (20 to 2 mm Hg/100° C.) and is received in cooling traps. Substantially the entire amount of acetic acid anhydride is distilled off in about 6.5 hours.

The yield is 127.0 gram tin-(IV)-stearate.

EXAMPLE 7

This experiment was carried out in a 250 ml, four-neck flask fitted with thermometer, cooler and stirrer.
17.7 gram tin-(IV)-acetate and
90.4 gram montanic acid (aliphatic carboxylic acid with about 32 carbon atoms)
are introduced into the flask and the mixture is heated to 100° C. under slight vacuum conditions. At about 80° C. a yellowish melt is obtained. Thereafter acetic acid is removed by distillation under vacuum conditions at about 20 to 2 mm Hg/100° C. and is received in cooling traps (distillation time, about 6 hours). The acetic acid has been quantitatively distilled off in about 6 hours.

The yield is 96.2 gram tin-(IV)-montanate.

EXAMPLE 8

This experiment was carried out in a 250 ml, four-neck flask fitted with thermometer, distillation attachment and stirrer.
35.5 gram tin-(IV)-acetate and
46.5 gram caproic acid
are introduced into the flask and the mixture is heated under stirring to 110° C. After applying a slight vacuum, the acetic acid thus formed is removed by distillation and is received in a cooled receptacle. The reaction time amounted to about 2.5 hours.

The yield is 57.0 gram tin-(IV)-caproate.

EXAMPLE 9

This experiment was carried out in a 250 ml. 4-neck flask fitted with stirrer, distillation attachment and thermometer.

35.5 gram tin-(IV)-acetate and
58.5 gram 2-ethylhexane acid are added to the flask. The mixture is heated under stirring and slight vacuum conditions to 130° C. The acetic acid thus formed is distilled into a cooled receptacle. The reaction time amounted to about 3 hours.

The yield was 69.7 gram tin-(IV)-2-ethylhexanoate.

EXAMPLE 10

This experiment was carried out in a 500 ml. 4-neck flask fitted with stirrer, distillation attachment and thermometer.

35.5 gram tin-(IV)-acetate and
80.1 gram lauric acid were added to the flask. A slight vacuum is applied and the mixture is melted at about 60° C. and subsequently heated under stirring up to 100° C. The acetic acid thus obtained is received in a cooled receptacle. The reaction time amounts to about 2.5 hours, and the yield is 93.1 gram tin-(IV)-laurate.

EXAMPLE 11

This experiment was carried out in a 500 ml. 4-neck flask fitted with stirrer, distillation attachment and thermometer.

37.3 gram tin-(IV)-acetate and
143.1 gram behenic acid were added to the flask. The mixture is melted at about 80° C. under slight vacuum conditions and is further heated to 120° C. The acetic acid thus obtained was received in a cooled receptacle. The reaction time amounts to about 3 hours, and the yield is 156.2 gram tin-(IV)-behenate.

I claim:

1. A method for the production of anhydrous tin-(IV)-acetate which comprises reacting metallic tin in powder form or Sn-(II)-acetate with an excess amount of acetic acid anhydride while stirring and at temperatures of about between 50° to 150° C. and while passing oxygen through the reaction mixture or adding an oxygen yielding agent to the reaction mixture, whereby tin-(IV)-acetate is formed, and separating the tin-(IV)-acetate from the reaction mixture.

2. A method for the preparation of anhydrous tin-(IV)-carboxylate which comprises:
   (a) preparing a reaction mixture of metallic tin or Sn-(II)-acetate and an excess amount of acetic acid anhydride, stirring the reaction mixture at a temperature ranging from about between 50° to 150° C. while passing oxygen through the reaction mixture or adding an oxygen yielding agent to the reaction mixture to form tin-(IV)-acetate;
   (b) separating the tin-(IV)-acetate thus obtained from the reaction mixture;
   (c) reacting the tin-(IV)-acetate with a carboxylic acid having more than four carbon atoms or the corresponding acid anhydride at a temperature ranging from about between 80° to 150° C. to form anhydrous tin-(IV)-carboxylate; and
   (d) removing from the reaction mixture liberated acetic acid or acetic acid anhydride by distillation under vacuum conditions.

3. The method of claim 1, wherein the metallic tin of step (a) is in powder form.

4. The method of claim 1, wherein step (a) is carried out in the presence of acetic acid as solvent.

5. The method of claim 1, wherein step (a) is carried out at a temperature of about between the 80° and 130° C. while step (c) is carried out at a temperature of about between 100° to 110° C.

6. The method of claim 1, wherein said oxygen yielding agent is hydrogen peroxide solution, the water introduced into the reaction mixture by said solution being converted into acetic acid by the addition of acetic acid anhydride.

* * * * *